United States Patent
Srinivasan et al.

(10) Patent No.: US 8,031,929 B2
(45) Date of Patent: Oct. 4, 2011

(54) X-RAY INSPECTION OF SOLDER REFLOW IN HIGH-DENSITY PRINTED CIRCUIT BOARD APPLICATIONS

(75) Inventors: Govindarajan T. Srinivasan, Portsmouth, NH (US); Michael W. Hamblin, Stow, MA (US); Joseph F. Wrinn, Winchester, MA (US); Peter A. Reichert, Boston, MA (US)

(73) Assignee: Teradyne, Inc., North Reading, MA (US)

( * ) Notice: Subject to any disclaimer, the term of this patent is extended or adjusted under 35 U.S.C. 154(b) by 672 days.

(21) Appl. No.: 12/190,035

(22) Filed: Aug. 12, 2008

(65) Prior Publication Data

US 2009/0080764 A1    Mar. 26, 2009

Related U.S. Application Data (60) Provisional application No. 60/974,378, filed on Sep. 21, 2007.

(51) Int. Cl.
*G06K 9/00* (2006.01)
(52) U.S. Cl. .......... 382/141; 382/144; 382/145
(58) Field of Classification Search ........ 382/141–158
See application file for complete search history.

(56) References Cited

U.S. PATENT DOCUMENTS

| | | | | |
|---|---|---|---|---|
| 4,523,838 A | * | 6/1985 | Yamada | 355/66 |
| 5,268,954 A | * | 12/1993 | Middleton | 378/85 |
| 5,481,585 A | * | 1/1996 | Kimura et al. | 378/134 |
| 5,621,811 A | | 4/1997 | Roder et al. | |
| 6,748,046 B2 | | 6/2004 | Thayer | |
| 6,748,378 B1 | | 6/2004 | Lavender et al. | |
| 6,917,668 B2 | | 7/2005 | Griffith | |
| 7,013,038 B1 | | 3/2006 | Patnaik | |
| 2007/0122020 A1 | | 5/2007 | Claus | |

OTHER PUBLICATIONS

International Search Report and Written Opinion for Application No. PCT/US2008/076965 mailed on Apr. 17, 2009.

* cited by examiner

*Primary Examiner* — Michael P Stafira
(74) *Attorney, Agent, or Firm* — Wolf, Greenfield & Sacks, P.C.

(57) ABSTRACT

According to one embodiment, a method for processing one or more X-ray images includes: receiving at least one image of the one or more X-ray images, the one or more X-ray images being of an assembly extending along a plane; based on the at least one image, autonomously determining a respective displacement value for each of portions of the assembly with respect to one or more directions of the plane, each of the displacement values being determined relative to a respective actual value; storing the displacement values; and applying a rule to the stored displacement values, the rule being for determining a defect status of the assembly.

19 Claims, 10 Drawing Sheets

X-RAY INSPECTION OF SOLDER REFLOW IN HIGH-DENSITY PRINTED CIRCUIT BOARD APPLICATIONS

CROSS-REFERENCE TO RELATED PATENT APPLICATIONS

This application claims priority to U.S. Provisional Patent Application No. 60/974,378, filed on Sep. 21, 2007, the content of which is incorporated herein by reference in its entirety.

BACKGROUND OF THE INVENTION

Embodiments of the present invention relate generally to image inspection systems and methods, and more particularly to an X-ray inspection system using tomosynthesis imaging techniques.

An image system may be used to inspect assemblies such as printed circuit boards (PCBs). PCBs may have connectors such as ball grid arrays (BGA) or column grid arrays (CGA). Examples of such connectors include the NeXLev® high-density parallel board connectors commercially available from Amphenol Corp. of Wallingford, Conn. These connectors are increasingly being used in PCB applications because they allow electronic design engineers to relocate high pin count devices onto a mezzanine or module card to simplify board routing without compromising system performance. Currently, there are about fourteen different types of high-density parallel board (i.e., NeXLev®-like) connectors in the PCB industry.

A PCB on which a BGA is present may be inspected for defects. Pins on a BGA may be deemed defective when solder does not reflow properly (or correctly) during manufacturing and/or where the solder reflow process is similarly deficient or otherwise insufficient. As a result, defects such as bridges and ball-and-socket-type opens may be present. The presence of such defects at or on any one pin will generally result in the failure of an entire connector on a multi-connector board.

The inspection of high-density parallel board connectors, such as the NeXLev® connectors, may involve several difficulties. At least some of these difficulties are related to: the impacts of the reflow process on the connectors; obscuration and associated artifacts produced by the connector blade; often subtle differences between non-defective (or acceptable) and defective (or unacceptable) solder balls; and the staggered positioning of solder balls in some BGAs.

SUMMARY OF THE INVENTION

An aspect of embodiments of the present invention is directed to more accurately identifying defective portions (e.g., pins) of electronic assemblies based on images of the assemblies taken using X-ray imaging techniques.

According to one embodiment, a method for processing one or more X-ray images includes: receiving at least one image of the one or more X-ray images, the one or more X-ray images being of an assembly extending along a plane; based on the at least one image, autonomously determining a respective displacement value for each of portions of the assembly with respect to one or more directions of the plane, each of the displacement values being determined relative to a respective actual value; storing the displacement values; and applying a rule to the stored displacement values, the rule being for determining a defect status of the assembly.

According to another embodiment, a system for processing one or more X-ray images includes: means for receiving at least one image of the one or more X-ray images, the one or more X-ray images being of an assembly extending along a plane; means for, based on the at least one image, autonomously determining a respective displacement value for each of portions of the assembly with respect to one or more directions of the plane, each of the displacement values being determined relative to a respective actual value; means for storing the displacement values; and means for applying a rule to the stored displacement values, the rule being for determining a defect status of the assembly.

BRIEF DESCRIPTION OF THE DRAWINGS

For a better understanding of the invention as well as other objects and further features thereof, reference is made to the following detailed description of various preferred embodiments thereof taken in conjunction with the accompanying drawings (which are not to scale) wherein.

DETAILED DESCRIPTION OF THE PREFERRED EMBODIMENTS

Embodiments of the present invention are directed to systems for inspecting electronic assemblies such as, but not limited to, circuit cards and printed circuit boards (PCBs). In particular embodiments, the systems may be used to inspect PCBs on which ball grid arrays (BGAs) are present. In particular embodiments, the system is (or is similar to) an X-ray inspection system, for example, operated according to a tomosynthesis imaging technique. Such a technique is disclosed in U.S. Pat. No. 6,748,046 to Thayer, the content of which is incorporated herein by reference in its entirety.

Although certain embodiments are described herein with reference to inspection systems using X-ray energy, other embodiments may be applied in other contexts including, but not limited to, inspection, imaging, and/or test systems employing X-rays or other suitable forms of electromagnetic energy.

Figure 1A:
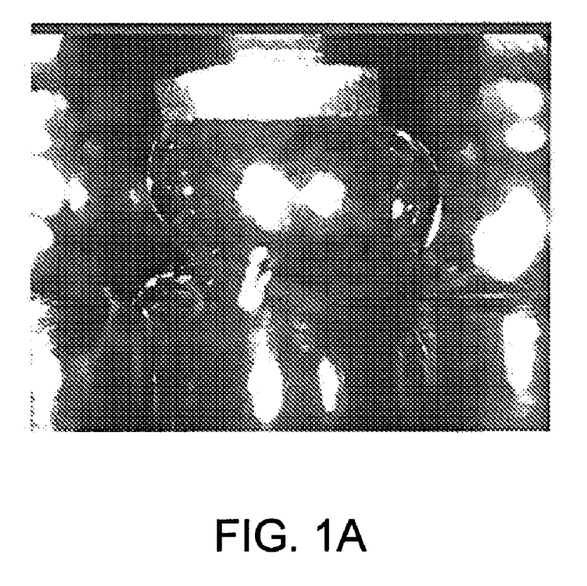
FIG. 1A is an optical image of an improperly (or incorrectly) reflowed ball grid array (BGA) solder ball on an exemplary NeXLev® connector.
Figure 1B:
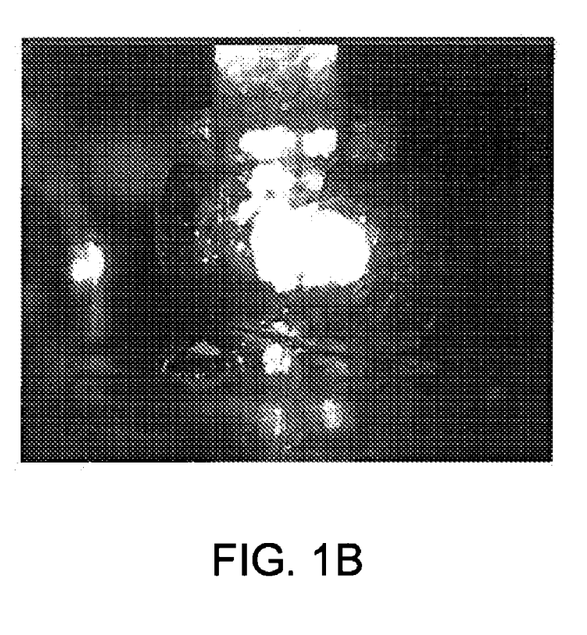
FIG. 1B is an optical image of another improperly reflowed BGA solder ball on an exemplary NeXLev® connector.

With reference to FIGS. 1A and 1B, two examples of defective solder balls in a NeXLev® connector are shown. The solder balls are not sufficiently symmetrical in shape but instead are somewhat elliptical or elongated along a plane (e.g., an x-y plane, which extends parallel to a surface of the PCB). A defective solder ball (or pin) is a ball which has not reflowed properly (or correctly) during manufacturing. In an X-ray image, a defective solder ball may appear shifted in position with respect to its neighbors (i.e., adjacent solder balls). Although the appearance of defects may be visibly noticeable in the marked drawings supplied herein, differences between the defective and non-defective solder balls may be quite subtle. For example, there may be a difference of only less than 10% between the shape of a defective solder ball and a non-defective (e.g., sufficiently symmetric) solder ball. As such, the difficulty of accurately detecting defects is increased.

As will be described in more detail below, an X-ray image of a ball-and-socket-type open defect may appear as a slight displacement from a center line of a row extending along an x-direction (see, for example, FIG. 6) or from that of a column extending along a y-direction (see, for example, FIG. 7) of a matrix (or matrix-like) arrangement or configuration.

Figure 1C:
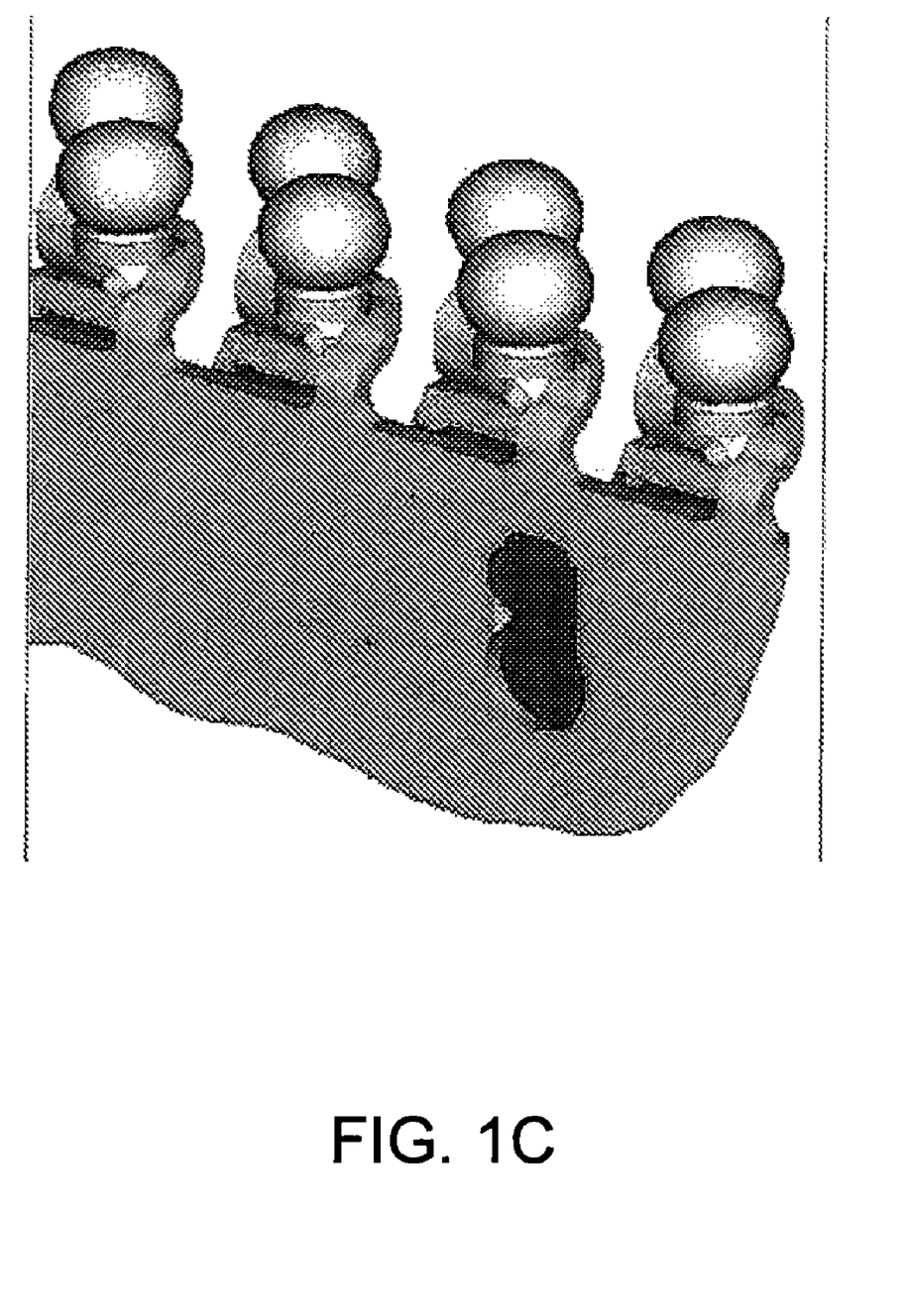
FIG. 1C is a schematic diagram of a perspective view of a portion of the pins of an exemplary NeXLev® high-density blade connector.
Figure 2:
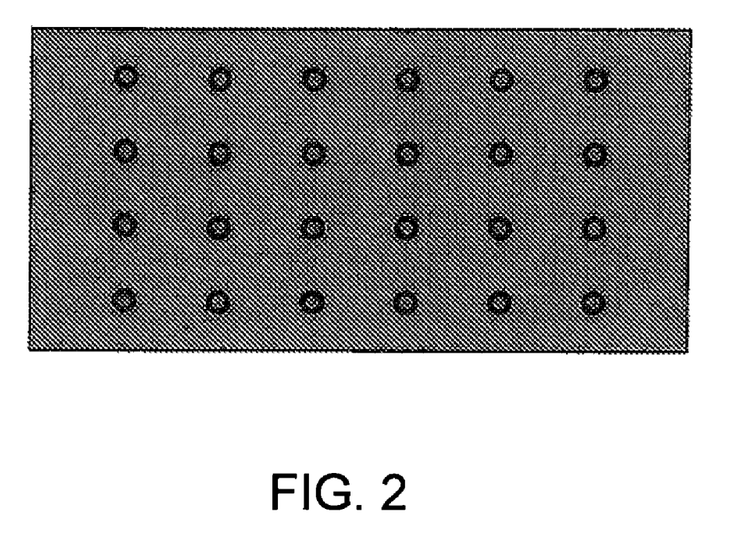
FIG. 2 is a schematic diagram of a planar view of a standard matrix pattern of an exemplary BGA in rows and columns.

Aspects of the present invention are directed towards identifying defective pins of BGAs and column grid arrays (CGAs) on connectors such as those described above, incurring minimum false calls and using X-ray imaging techniques. Here, difficulties arise due to factors such as the presence of high-density components and an insufficient angle of incidence of X-ray beams on the component being inspected. Further, obscuration from the NeXLev® connector blade may cause artifacts in an X-ray image of the connector that may also adversely affect detection of defects. With reference to FIG. 1C, a blade portion of a NeXLev® connector is shown. The curved light lines in FIG. 5, FIG. 6 and FIG. 7 (see, for example, the regions of FIG. 5 located within rectangles A and B) represent artifacts created by the connector blade. Detection may be further complicated by the arrangement matrix (staggered vs. normal matrix, as shown, for example, in FIG. 3 and FIG. 2, respectively) as used by manufacturers.

Known methods of detecting defects on these types of connectors have largely been unsuccessful, resulting in false call rates in excess of 60%. Such results increase costs, for example, for manufacturers who opt to use a manual X-ray imaging system in order to verify the results of an automated X-ray imaging system. Such manual X-ray systems require approximately two to three minutes to inspect a defective pin. Such a delay would incur significant slow downs in manufacturing (e.g., in or along a production line).

As such, an aspect of the present invention is directed towards accurately determining the defective pins on connectors including, but not limited to, those described above and towards minimizing (or at least reducing) the false call rates, thereby eliminating the need for a manual imaging system in addition to (or in place of) an automated imaging system.

According to embodiments of the present invention, defective pins—such as those that may have been the result of an improper (or incorrect) reflow process in the manufacturing of circuit board assemblies and subassemblies—are identified more accurately. According to exemplary embodiments, such defective pins are identified in BGA- or CGA-type connectors, such as the class of connectors referred to as NeXLev® connectors. The identification is performed to provide at least acceptable fault coverage and minimum (or reduced) false call rates.

Figure 3:
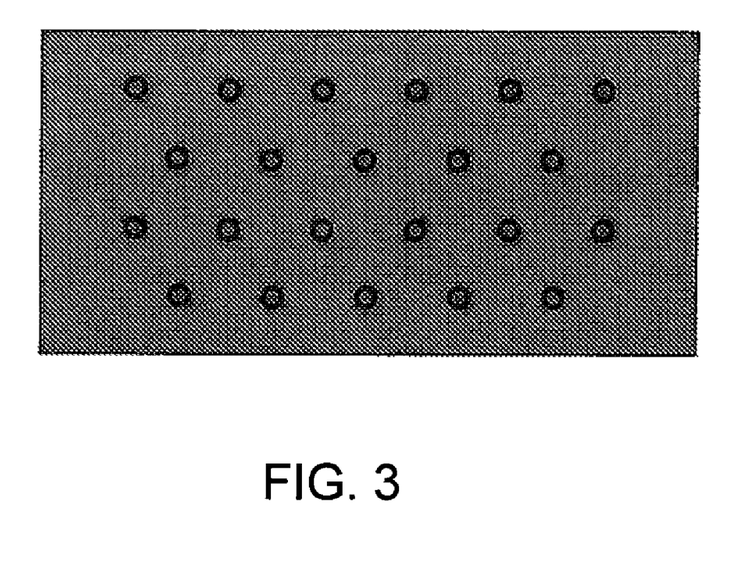
FIG. 3 is a schematic diagram of a planar view of a staggered pattern of an exemplary BGA in rows and columns.
Figure 5:
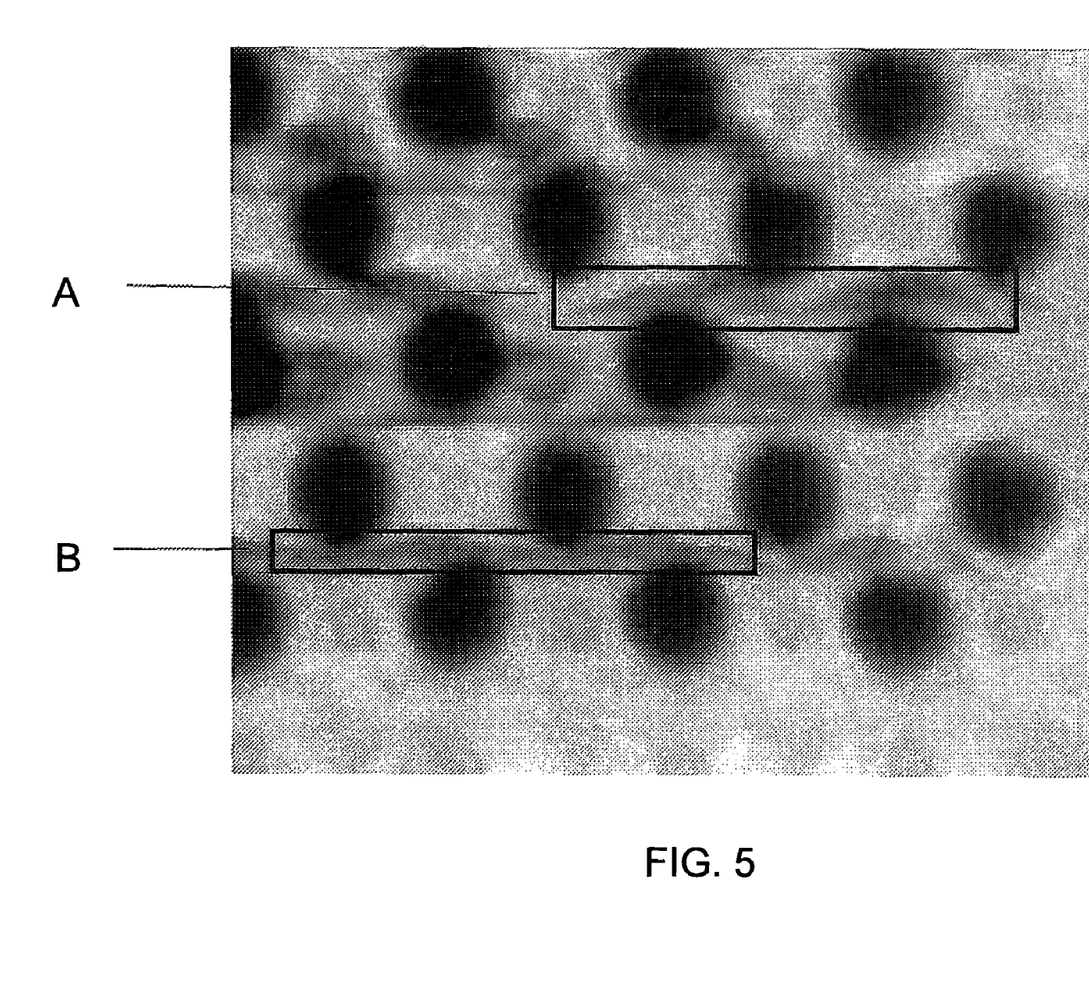
FIG. 5 is an X-ray image of a slice taken through a BGA of an exemplary NeXLev® connector having no defects.

As previously described, arrays of pins on such connectors may be arranged according to a regular matrix (see, for example, FIG. 2) or to a staggered matrix (see, for example, FIG. 3). With reference to FIG. 5, an X-ray image of a slice taken through a BGA of an exemplary NeXLev® connector is shown. The connector does not have any defects; however, it does have artifacts from the high density blades (see, for example, the regions of FIG. 5 located within rectangles A and B). As also previously described, such artifacts can obscure such images and hinder detection of defects.

Figure 4A:
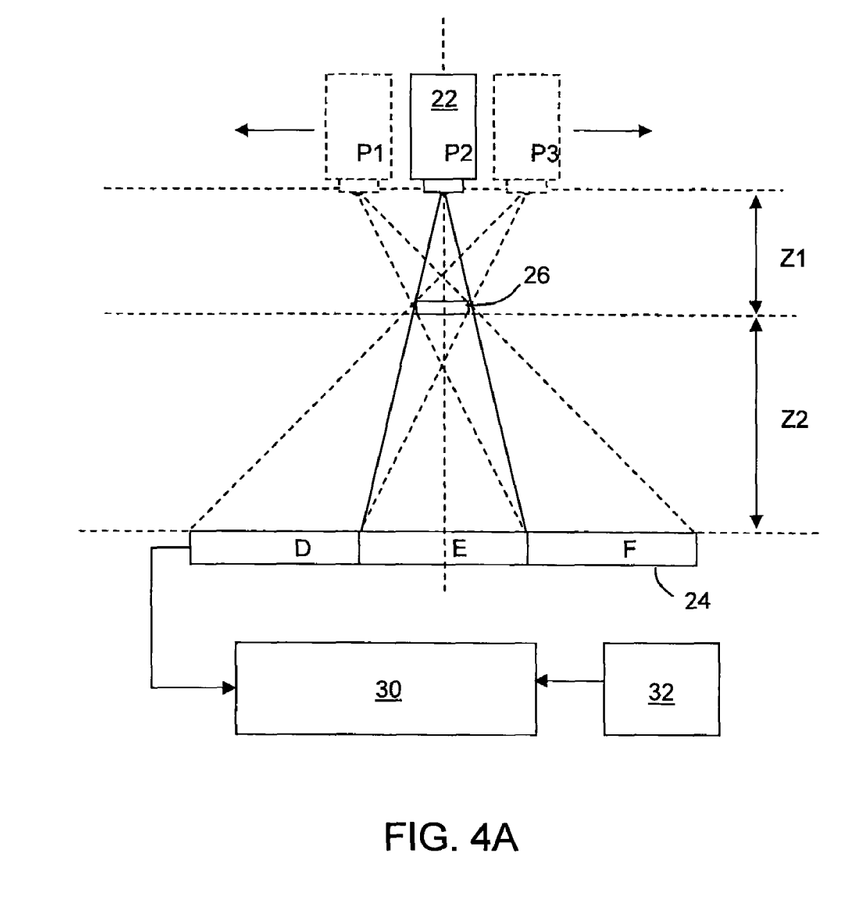
FIG. 4A is a schematic diagram of an X-ray inspection system according to an embodiment of the present invention.

With reference to FIG. 4A, an X-ray inspection system according to one embodiment is shown. The system includes an X-ray source 22 (such as, but not limited to, an X-ray tube) positioned opposite an X-ray detector 24. In one embodiment, the detector 24 is a detection panel including a plurality of pixels. The detection panel may be generally flat. In a particular embodiment, the detector 24 is composed of 2496× 2304 generally square-shaped pixels, each pixel having a length of approximately 50 μm.

An object 26 that is to be inspected (or imaged) is positioned at a reconstruction plane (or image plane) 23 located between the source 22 and the detector 24. With continued reference to FIG. 4A, the reconstruction plane 23 is spaced at a distance Z1 from the focal spot of the source 22 and at a distance Z2 from the detector 24. The distances Z1, Z2 may be adjusted to suitably provide a desired field of view (FOV) of the object 26. During inspection, a voltage (such as, but not limited to, a voltage of approximately 110 kilovolts) and a current (such as, but not limited to, a current ranging from approximately 0.070 milliamps to approximately 0.140 milliamps) are applied to the source 22 for producing X-ray energy. Accordingly, the source 22 produces X-ray energy, which penetrates or is absorbed by the object 26, and penetrating X-ray energy is detected by one or more region(s) of the detector 24.

Figure 9:
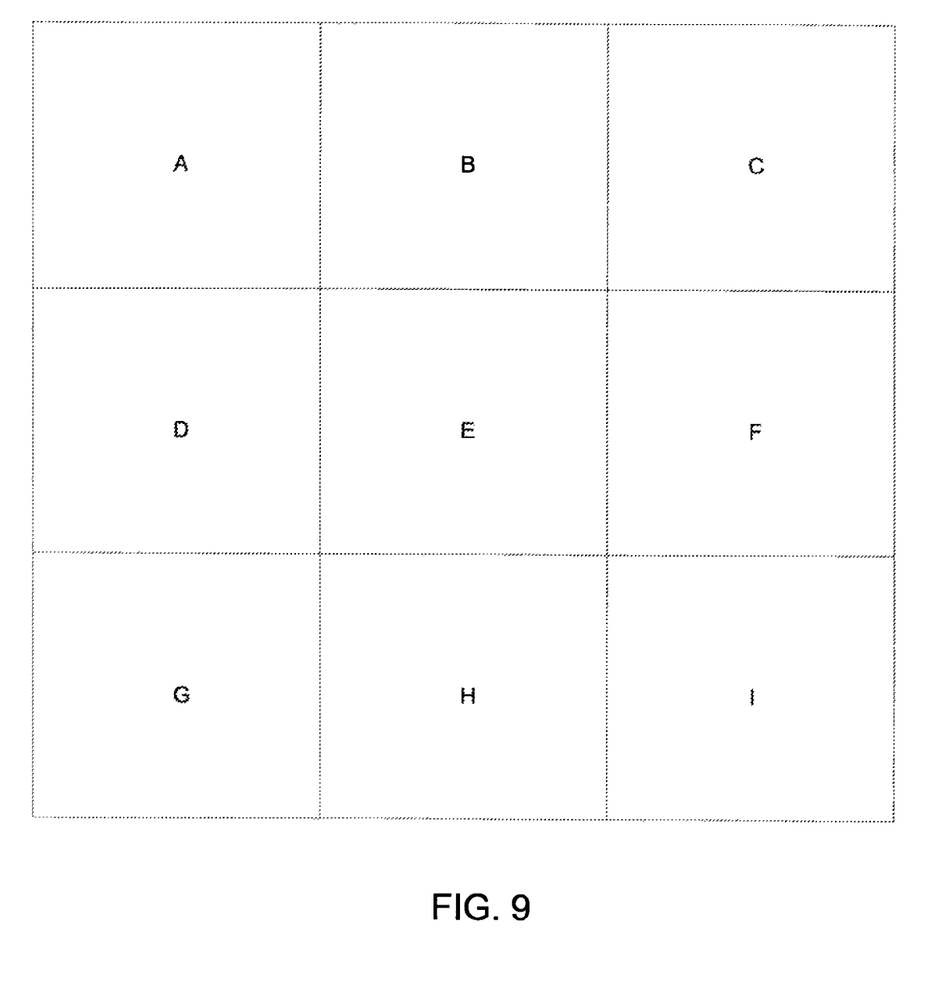
FIG. 9 is a schematic diagram of a "lawn mowing" pattern.

With reference to FIG. 4A, according to one embodiment, the source 22 may be moved to different positions (see, e.g., positions P1, P2, P3) with respect to object 26 to provide different views of the object 26. These different views may correspond to different respective images (see, for example, images D, E, F of FIG. 9). Here, the position of the object 26 is kept generally fixed, and the distance Z1 is kept constant as the source 22 is moved. Although FIG. 4A shows that the source 22 is moved generally along a first dimension (i.e., towards the left or the right in FIG. 4A), those skilled in the art will appreciate that the source 22 may also be moved generally along a dimension perpendicular to the first dimension (i.e., a direction pointing out from or into the figure) to provide different views of the object 26. For example, the source 22 may be positioned to produce the nine images A, B, C, D, E, F, G, H, I, as shown in FIG. 9.

Figure 4B:
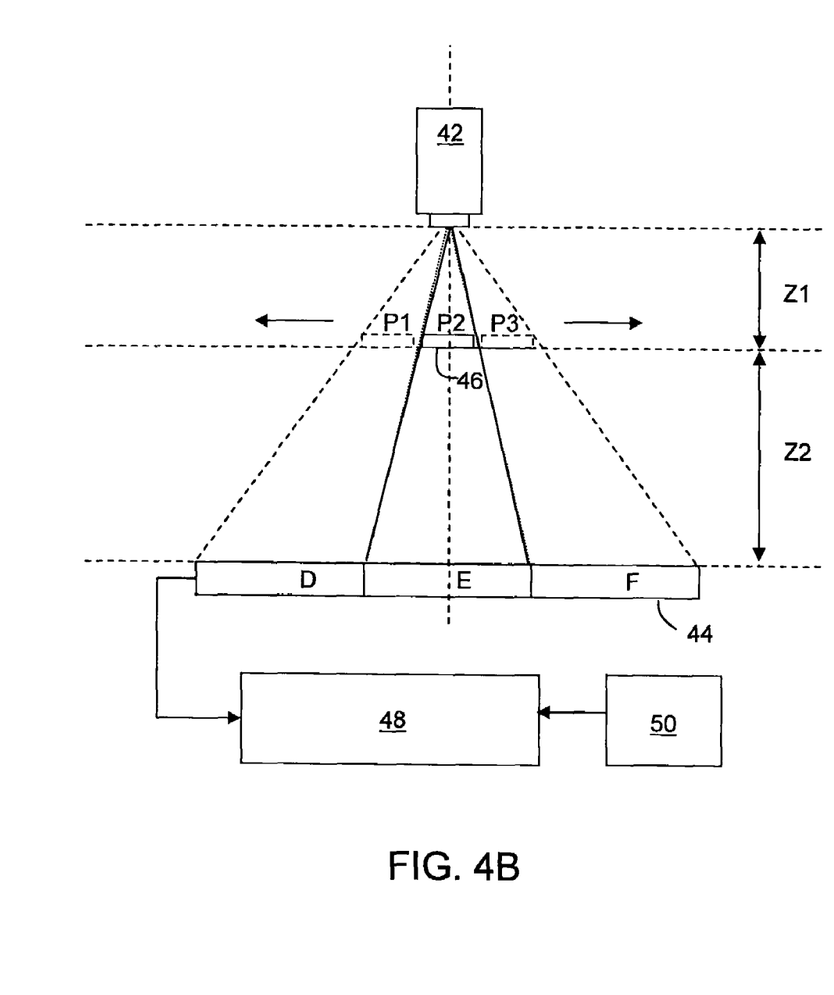
FIG. 4B is a schematic diagram illustrating of an X-ray inspection system according to another embodiment of the present invention.

With reference to FIG. 4B, according to another embodiment, the source 42 remains stationary, while the object 46 is moved generally along the dimensions described in the above paragraph (see, e.g., positions P1', P2', P3'). Similar to the embodiment of FIG. 4A, the detector 44 is positioned opposite the source 42.

In certain embodiments, the detector 24, 44 is a solid-state device that receives the penetrating X-ray energy (including X-ray energy attenuated by the object) and accordingly produces image data (including, but not limited to, grayscale image values) which may correspond to an image viewable to human eyes. In certain embodiments, the output values are sent to an image processor and/or viewer for processing and/or viewing (see, for example, processor/viewer 30 in FIG. 4A and processor/viewer 48 in FIG. 4B).

In certain embodiments, a beam monitoring device (see, for example, the monitoring device 32, 50 of FIG. 4A, 4B) may be used in addition to, or in place of, the detector. In a particular embodiment, the beam monitoring device is a photodiode. Similar to the detector 24, 44, the beam monitoring device is for detecting X-ray energy. In certain embodiments, the beam monitoring device is coupled with the processor/viewer 30, 48. As such, it is understood that measurements provided by the detector 24, 44, as described above, may also be provided by the beam monitoring device.

Figure 8:
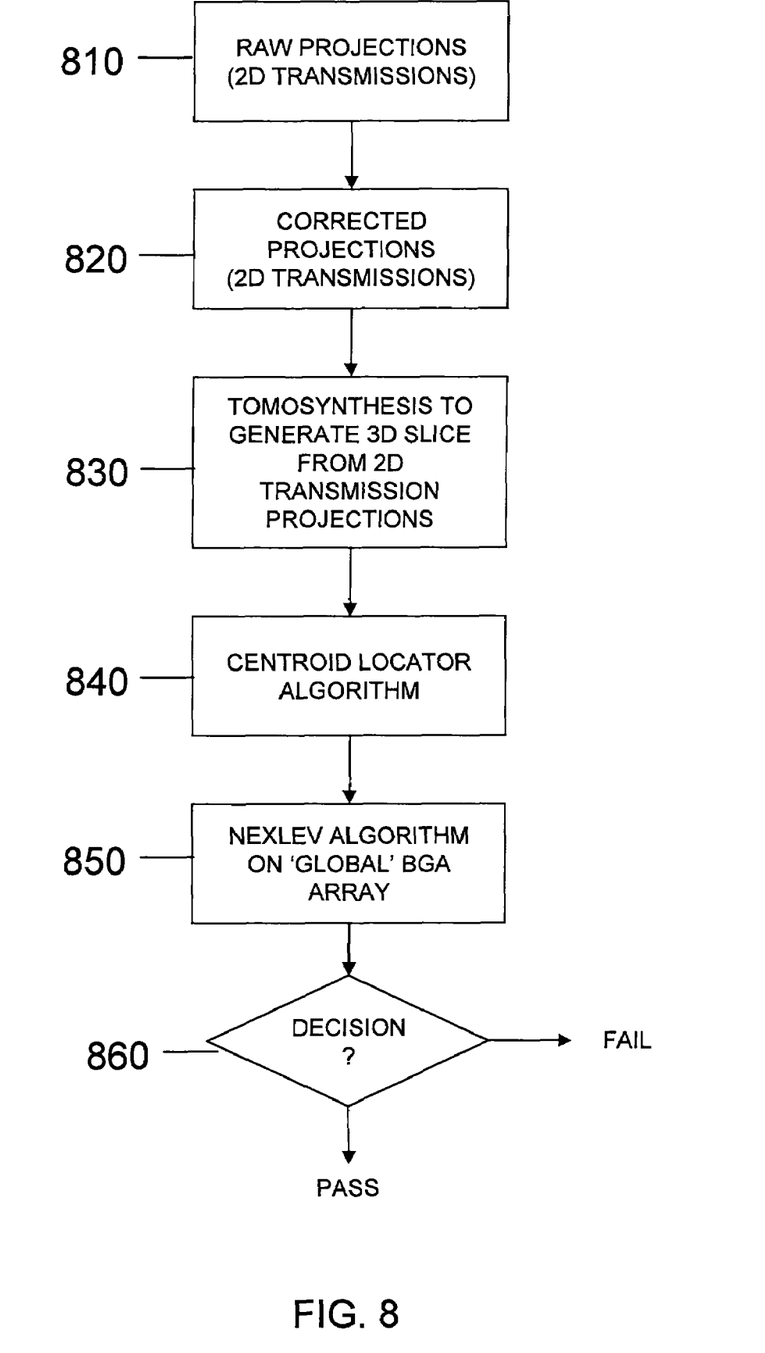
FIG. 8 is a flow diagram of an inspection process according to an embodiment of the present invention.

With reference to FIG. 8, a flow diagram of a process, for identifying defective pins, according to an embodiment of the present invention, is shown. The process uses images including, but not limited to, images produced using X-ray imaging, as described above. According to certain embodiments, this process may be implemented in programmed instructions executed on a computer system.

According to an embodiment of the present invention, multiple X-ray images are obtained of a region of interest (ROI) of a target device or object (see, for example object 26, 46 of FIG. 4A, 4B). Each X-ray image is in the form of a 2-dimensional transmission image, referred to herein as a "projection." According to an exemplary embodiment, the projections are obtained using the system configurations illustrated in FIG. 4A and/or FIG. 4B.

An image obtained using such a system may likely include some undesirable artifacts. These artifacts may result from imperfections of the detector response due to dark current, nonlinear exposure of the detector by the X-rays, the nature and/or behavioral characteristics of the detector, and/or perhaps some other offset(s). In order to remove or at least partially compensate for one or more of these undesirable artifacts, the two-dimensional image of the projections is corrected. The corrected images are used to generate a three-dimensional image representing a "slice" taken through the ROI of the target device. The slice may not align perfectly (or exactly) with any of the two-dimensional images already taken. Therefore, the three-dimensional image may be reconstructed using tomographic techniques, as will be described in more detail below. According to embodiments in which the ROI corresponds to a BGA, or a similar arrangement of pins (or solder balls), the three-dimensional slice is taken through an array of solder balls, e.g., parallel to a printed circuit board at a certain height (e.g., a height z) between the surface of the board and an end of the pin.

In such embodiments, a suitable image processing algorithm may be used to locate a centroid of each of the solder balls within the 3-dimensional slice. The corrected slice image and the results of the centroid locator are used to determine from the image whether an improper (or incorrect) solder reflow process may have occurred during assembly or manufacture of the device.

An exemplary embodiment will now be described in more detail with reference to FIG. 8.

As shown in box 810, one or more raw 2-dimensional X-ray transmission images of the board under inspection are obtained using an X-ray imaging system, such as, but not limited to, the systems described earlier. In one embodiment, nine such images (see, for example, FIG. 9) are acquired using the 'lawn mowing' tomosynthesis acquisition methodology, which is described in more detail in U.S. Pat. No. 6,748,046 to Thayer, as previously noted. For example, the relative position of a device in the image plane of an X-ray imaging system with respect to a source is varied to obtain nine different 2-dimensional X-ray images having the rectangular grid arrangement (images A, B, C, D, E, F, G, H and I), as illustrated in FIG. 9. One of the images (e.g., image E) is taken with the device directly between the X-ray source and sensor. The other eight images are taken with the X-ray source at different respective angles with respect to the device.

More generally, classical digital radiography techniques rely on X-ray flux to distinguish high contrast features. Tomosynthesis techniques rely on X-ray flux measurements taken from different angles (or views) to form an image using a density map of an object. Here, at each angle, the performance of the measurement is essentially identical (or similar) to taking a conventional X-ray image.)

As previously noted, two-dimensional raw images produced by X-ray systems such as those described herein are referred to in this disclosure as projections. Projections may be calibrated (or corrected), for example, to remove artifacts including, but not limited to, undesirable artifacts of the X-ray imaging process. For example, the projections may be field flattened and the image data linearized with respect to thickness of object measured. Field flattening is performed to ensure that there is a more uniform representation of data at the edges (or edge portions) of the image relative to the center (or center portions) of the image. As such, field flattening improves homogeneity of the image.

According to one embodiment, correction of the image(s) is performed (see, for example, box 820 of FIG. 8). The correction may include field flattening of the image, as described in more detail below.

If I(i, j) represents the 2-dimensional raw projection image (i.e., with i, j referring to a particular pixel of the detector and I(i, j) referring to the grayscale value produced by that pixel), then field flattening yields a corrected image $I_{corrected}$ that may be expressed as $$I_{corrected}(i,j) = (I(i,j) - I_{dark}(i,j)) \times B(i,j) + \text{Offset}(i,j). \quad (1)$$

The subtraction of $I_{dark}(i,j)$ is performed to correct or adjust for dark current that may exist in the particular X-ray sensor (or detector) used. The dark intensity is derived from one or more dark images, which are taken, for example, at a drive voltage of around 0 kilovolts and a drive current of around 0 milliamps. As such, dark images are images taken in the absence of X-ray energy.

With continued reference to equation (1), B(i, j) refers to a gain value computed by shooting X-rays at a known energy (e.g., at a known drive voltage and drive current) through multiple plates of a known material (e.g., stainless steel) one plate at a time. The plates have different thicknesses with respect to one another. For example, three different plates may be used (e.g., a plate of a lower thickness, one of a medium thickness, and one of a higher thickness). For example, respective thicknesses of the plates may be 5 mils, 15 mils, and 30 mils. Once measurements have been taken of the different plates using the X-rays of a known energy, the results may be used to derive a linear curve fit. The linear curve fit is derived to approximate the non-linear response of X-ray intensity with respect to the thickness of the sample measured. That is, the relationship between the intensity values and the thickness of the inspected object may be approximated by a linear equation of the form y=mx+c (see, for example, equation (1) above). In such an equation, m is the slope of the curve and c is the y-offset.

After the dark image correction is performed, then a digital gamma correction may be performed. The $I_{corrected}(i,j)$ projection image may be further processed using standard image processing techniques. One such technique is known as gamma processing. Here, the corrected projection image is input into a gamma function. The result is an image having a more uniform variation of intensity within a given grayscale range. Mathematically, such processing may be represented by equation (2) below:

$$I_{\gamma corrected}(i,j) = \gamma_{index}(I_{corrected}(i,j)). \quad (2)$$

Further corrections may also be made. For example, if one or more pixels of a digitizing X-ray sensor are known in advance to be defective (or otherwise imperfect) (e.g., in some situations, a map may be provided identifying such pixels), these pixels may be corrected for. For example, an image value may be ascribed to a defective pixel, where the ascribed value is based on a weighted interpolation of neighboring pixels. Such correction may be useful in that values in the projection data, that are produced by defective pixels, may be removed and replaced. The resulting corrected image is referred to herein as $I_{final}(i,j)$.

$$I_{final}(i,j) = \text{Detector correction}(I_{\gamma corrected}(i,j)) \quad (3)$$

The above-described correction of the image (see, for example, box 820 of FIG. 8) may be repeated for each of the multiple 2-dimensional transmission images produced. Therefore, according to one embodiment, in which a total of nine images are produced, the resulting corrected images may be referred to as $I_{final\_k}(i,j)$, where the value of k ranges from 0 to 8. These images represent input images for the further processing described below.

With continued reference to FIG. 8 (see, for example, box 830 of FIG. 8), in one embodiment, the corrected projection images $I_{final\_k}(i,j)$ are then provided to a tomographic processor. The processor performs a tomosynthesis reconstruction using suitable techniques to obtain a 3-dimensional description of the imaged device. This 3-dimensional description may be used to obtain a 3-dimensional slice generated from the nine 2-dimensional corrected projections (referred to herein as a 3-dimensional slice), in which the resulting slice is provided having a different angle (or perspective) with respect to the device geometry relative to any of the nine 2-dimensional corrected projections. According to an exemplary embodiment, such a slice is provided to have an angle parallel to the surface of a printed circuit board upon which a component is mounted. In a particular embodiment, the slice is determined to extend along a parallel plane that includes the array of pins (or reflowed solder balls)—e.g., the BGA. Such tomographic processing may use vector calculations in the X plane (Rvectorx) and Y plane (Rvectory) for effectively shifting the field of view of each of the 8 off-axis projections into the field of view of the original on-axis projection (see, for example, FIG. 9).

With reference to FIG. 5, an image of a BGA provided by an exemplary 3-dimensional slice generated using the above principles is shown. The 3-dimensional slice is obtained at a selectable height above a surface of the PCB (e.g., midway between the surface of the PCB and the adjacent ends of the pins). According to an exemplary embodiment, such images showing the BGA are further analyzed, for example, for identifying any incorrect reflow.

Current algorithms have relied on a ball-by-ball analysis. For example, specific regions of a 3-dimensional slice have been further analyzed locally to determine features of each solder ball or pin, such as its centroid, diameter, moment ratio (i.e., a ratio of the major axis to the minor axis of elliptically shaped balls), and other characteristics of each ball or pin in the slice.

According to an embodiment of the present invention, features and/or characteristics (such as, but not limited to, those features described above) of two or more of the solder balls are analyzed concurrently and/or more collectively. According to a particular embodiment, the characteristics of an entire row (or column) of the BGA array are computed. As such, the features are analyzed more globally (or collectively) to assess the presence of manufacturing errors such as, but not limited to, improper solder reflow. For example, values of such features are compared to other values (e.g., measured or expected values) to produce a set of displacement values. Calculations based on the displacement values are then used to assess the presence of the manufacturing errors.

With reference to FIG. 8 (see, for example, box 840 of FIG. 8), according to an exemplary embodiment, centroids (i.e., the center of mass) of the solder balls are analyzed in further detail. In more detail, a suitable centroid algorithm is used to determine a center of mass of each ball or pin in the array.

According to one embodiment, a center of mass of a ball (or pin) is determined by creating an ROI surrounding the image of the ball. The grayscale image value of each pixel within the ROI is analyzed. For example, the grayscale image values are analyzed to determine whether they fall within a certain range (i.e., between a certain low threshold and a certain high threshold). Those skilled in the art can appreciate that centroid values may be calculated using the number of and locations (or coordinates) of pixels that have grayscale image values that fall within the range.

The centroid values may be stored for further processing. For example, each of the values may be stored in a two-dimensional array at a row and column corresponding to the position of the solder ball in the x-y plane of the particular 3-dimensional reconstructed slice.

After the centroid values are stored, the values may be analyzed collectively (see, for example, box 850 of FIG. 8), as will be described in more detail below. Here, a displacement algorithm may be used to determine displacement of each centroid determined above in the 3-dimensional slice.

First, according to one embodiment, an inspection list may be used to identify the actual center x and y location of each of the pins in the BGA array. According to one particular embodiment, these values may be determined from a physical inspection of the geometry (e.g., a measurement) of the array. According to another particular embodiment, these values may be determined from specifications (drawings) of the device. For example, the values may be refer to center coordinates as specified in a computer-assisted design (CAD) specification for the device. The actual values (as described above) may be different from the centroid values (also previously described) due to manufacturing errors or imperfections. As will be described in more detail below, differences (e.g., deviations or displacements) of the centroid values with respect to the actual values may be calculated and analyzed. The actual x-y locations of the pins may be represented by the values $P_{actual}(x,y)$. Similar to the centroid values, these values may also be stored in an array.

A deviation (or displacement) of the centroid (as described above) of each of the pins or solder balls in the array relative to the actual locations ($P_{actual}(x,y)$, as also described above) may then be determined. The results may be referred to as actual displacement-per-pin ($P_{disp}(x,y)$) and may be mathematically represented by equation (4) below:

$$P_{disp}(x,y) = \text{centroid}(P_{actual}(x,y)) - P_{actual}(x,y). \quad (4)$$

These displacement values may be stored for further processing. In some embodiments, absolute values of one or more of the displacement values may be used for further processing. According to further embodiments, the values may be used to generate a histogram. For example, a histogram may be generated by adding into respective bins of a histogram, the values $P_{disp}(x,y)$ determined for each row $P_{binrow}(x',y)$ and each column $P_{bincolumn}(x,y')$ according to the values $P_{actual}(x,y)$, which were described earlier. Thus, two histograms are formed: one for rows of the array and the other for columns of the array. As such, the domain of a histogram may represent a particular row or column.

A running total of the displacement values may be maintained for pins located within each of the displacement bin locations (e.g., a given row or column location of a BGA). For example, a sum of all the $P_{disp}(x,y)$ values in a given row (see, for example, row x=5, which corresponds to a top-most row in the configuration of FIG. 5) is calculated and stored in a bin 5 corresponding to row 5 in a histogram maintained for the rows of the device. This process may be repeated for each of the other rows of the array, with the results stored in the respective bins of the row histogram.

Similarly, separate sums may also be maintained for the columns of the BGA. That is, a sum of all the $P_{disp}(x,y)$ values in a given column (see, for example, column y=1, representing a left-most column in the configuration of FIG. 5) is calculated. This process may also be repeated for each column of the array, with the results stored in the respective bins of the column histogram.

A respective average value of the histogram results may then be obtained for each row of the array. For example, an average may be computed for each x' (row bin value) as expressed in equation (5) below:

$$P_{avg\_rowbin} = \frac{\sum_{x'=1}^{N} P_{binrow}(x', y)}{N}. \quad (5)$$

Similarly, a respective average value of the histogram results may then be obtained for each column of the array. For example, an average may be computed for each y' (column bin value) as expressed in equation (6) below:

$$P_{avg\_columnbin} = \frac{\sum_{y'=1}^{N} P_{bincolum}(x, y')}{N}. \quad (6)$$

A residual displacement value may be determined using the computed average above for each pin P(x,y) in the array. For example, residual displacement values for each row of the array may be calculated according to equation (7) below:

$$P_{residual\_y}(x,y) = P(x,y) - \text{respective bin average } P_{binrow}(x',y). \quad (7)$$

Similarly, residual displacement values for each column of the array may be calculated according to equation (8) below:

$$P_{residual\_x}(x,y) = P(x,y) - \text{respective bin average } P_{bincolumn}(x,y'). \quad (8)$$

The distribution of residual x and/or y values, as described above, may be stored for each pin in the array and used for further processing. As such, similar to a low pass filtering process, noise can effectively be removed (or at least partially dampened). The removal of the noise may aid the identification of defects.

Figure 6:
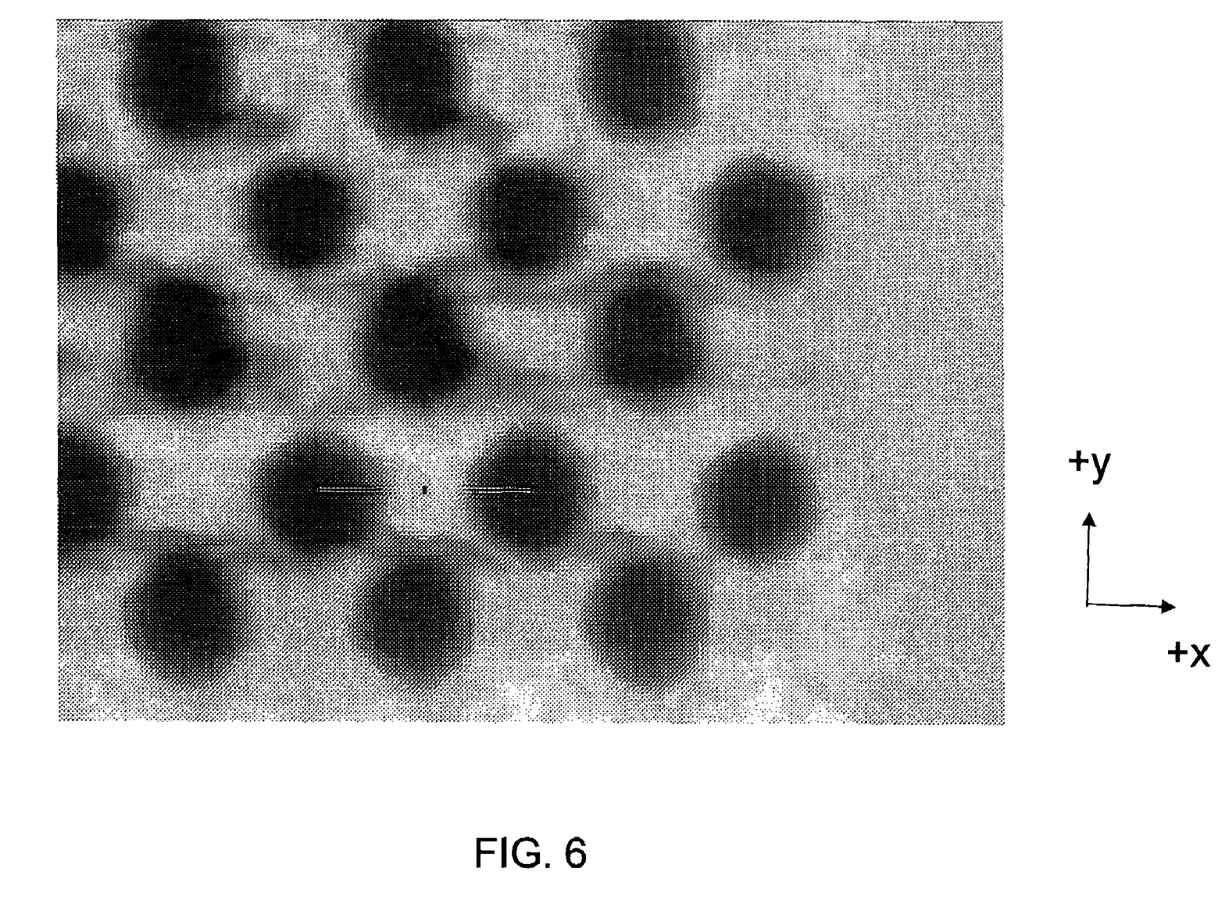
FIG. 6 is an X-ray image of a slice taken through a BGA of an exemplary NeXLev® connector having at least one reflow defect along a row direction.

According to one embodiment, comparing the distribution against one or given rules (or conditions) may be used to determine whether the imaged object is acceptable or unacceptable (see, for example, box 860 of FIG. 8). For example, according to one embodiment, a rule may be based on the distribution of the residual values along a certain direction(s) (see, for example, the positive and negative x direction, as shown in FIG. 6). Here, the rule may effectively test whether the residual values derived along this direction exceed a threshold amount or value and/or whether they fall within a certain range of values. Alternatively or in addition, a rule may be based on the distribution of the residual values in the positive and negative y direction (see, for example, FIG. 7). Such a rule may also effectively test whether the residual values derived along this direction exceed a threshold amount or value and/or whether they fall within a certain range of values. As such, the rules may be tailored to be suitable for a particular application and/or tolerance. With reference to FIG. 8, an indication such as, but not limited to, a user display is provided to inform a user of the rule result (e.g., pass, fail).

The specifics and/or requirements of the rule (such as, but not limited to, the threshold values or ranges described above) may be selected (or effectively selected) by the user according to the object that was imaged. For example, the rule may include one or more tolerable values of residual displacement in one or more directions (e.g., the x and y directions) for a given BGA configuration, component, or circuit.

As described above, in embodiments of the present invention, the acceptability of a given configuration, component or circuit is effectively assessed by identifying defective portions (e.g., pins), the distribution of which may exceed or be "further out" from that of portions deemed to be acceptable or tolerable.

As also described above, other aspects of the present invention are directed towards ensuring (or increasing the likelihood) that all of the defective pins are found without any "escapes" (e.g., events in which a system or process ought to identify a certain defect but fails to do so), while also yielding very minimal (or at least reduced) false call rates.

Referring to FIG. 6, a 3-dimensional X-ray slice image of BGA solder balls in a NeXLev® connector includes an unacceptable reflow defect in the row direction (i.e., the x direction of FIG. 6). Such a slice represents an exemplary output image (i.e., $I_{final}(i,j)$, as formulated in equation (3) above). A white line drawn between two pins in FIG. 6 indicates the distance between the good pin (the left-most pin of the pair) and the defective pin (the right-most pin of the pair).

Figure 7:
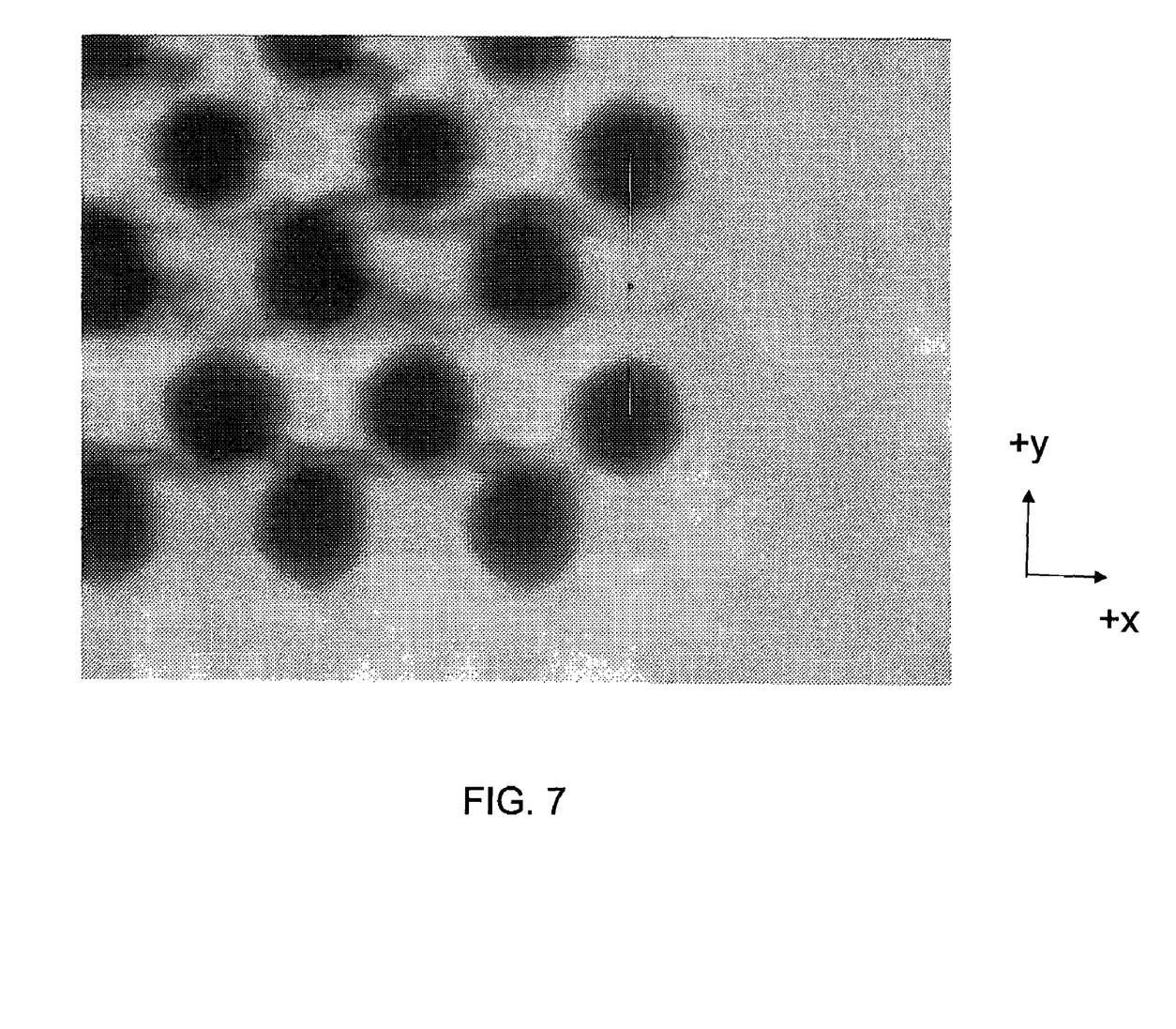
FIG. 7 is an X-ray image of a slice taken through a BGA of an exemplary NeXLev® connector having at least one reflow defect along a column direction.

Referring to FIG. 7, a 3-dimensional X-ray slice image of BGA solder balls in a NeXLev® connector includes an unacceptable reflow defect in the column direction (i.e., the y direction of FIG. 7). A white line drawn between two pins in FIG. 7 indicates the distance between the good pin (the upper pin of the pair) and the defective pin (the lower pin of the pair).

According to a further embodiment, evaluative processes (such as processes described above with reference to FIG. 8) may be repeated upon obtaining additional tomographic slices from the same X-ray images. For example, additional slices may be obtained representing images of the BGA in parallel planes located at different respective heights measured from a surface of the PCB. Thus, multiple 3-dimensional slices are obtained at different heights. The evaluative processes may be repeated for each of the different heights to identify defects according to rules, as described above. Additional rules may be provided based on the results of the multiple images.

According to an exemplary embodiment, three 3-dimensional slices are obtained at three different heights between the PCB surface and adjacent ends of the pins of a BGA (e.g., at 15 mils and 15 mils+/−5 mils for a spacing of 30 mils). Defects are determined independently for each of the pins in each of the different slices. Here, a majority voting rule may be applied to declare a defect, i.e., the PCB is deemed to be unacceptable only when defects are identified in two or more of the three different slices. As such, the reporting of false calls may be further reduced.

Although the invention has been described in detail with respect to various preferred embodiments, it is not intended to be limited thereto. For example, although certain embodiments have been described with respect to histograms, embodiments of the present invention are not limited thereto. Rather those skilled in the art will recognize that variations and modifications (such as other types of mathematical structures) are possible and are within the spirit of the invention and the scope of the appended claims.

What is claimed is:

1. A method for processing one or more X-ray images, the method comprising:
   receiving at least one image of the one or more X-ray images, the one or more X-ray images being of an assembly extending along a plane;
   based on the at least one image, autonomously determining a respective displacement value for each of portions of the assembly with respect to one or more directions of the plane, each of the displacement values being determined relative to a respective actual value;
   storing the displacement values; and
   applying a rule to the stored displacement values, the rule being for determining a defect status of the assembly.

2. The method of claim 1, wherein receiving the at least one image of the one or more X-ray images comprises:
   receiving a first image and a second image of the one or more X-ray images, wherein the at least one image and the at least a second image correspond to 2-dimensional X-ray images providing different view angles measured with respect to a perpendicular to the plane; and
   tomographically processing the received first image and second image, said processing resulting in a processed X-ray image.

3. The method of claim 1, whether storing the displacement values comprises storing the displacement values in a histogram.

4. The method of claim 1, wherein the rule is for determining whether the assembly meets a defined manufacturing tolerance.

5. The method of claim 1, further comprising autonomously providing a user indication as to a result of applying the rule.

6. The method of claim 1, wherein autonomously determining the displacement values comprises:
   determining a measured location for each of the portions of the assembly, with reference to the one or more directions of the plane;
   determining for each of the portions of the assembly an actual location with reference to the one or more directions of the plane; and
   determining for each of the portions of the assembly a difference between the measured and actual locations, the difference being indicative of the corresponding displacement value.

7. The method of claim 6, wherein determining the measured locations comprises determining for each of the portions of the assembly a centroid value of the portion.

8. The method of claim 6, wherein determining the actual locations comprises using a computer-aided design (CAD) specification of the assembly.

9. The method of claim 1,
   wherein the assembly is a ball grid array (BGA) assembly, and
   wherein the portions of the assembly correspond to solder balls of the BGA assembly.

10. A system for processing X-ray images, comprising an image processor configured to implement the method of claim 1.

11. A system for processing one or more X-ray images, the system comprising:
    means for receiving at least one image of the one or more X-ray images, the one or more X-ray images being of an assembly extending along a plane;
    means for, based on the at least one image, autonomously determining a respective displacement value for each of portions of the assembly with respect to one or more directions of the plane, each of the displacement values being determined relative to a respective actual value;
    means for storing the displacement values; and
    means for applying a rule to the stored displacement values, the rule being for determining a defect status of the assembly.

12. The system of claim 11, wherein the means for receiving is configured for:
    receiving a first image and a second image of the one or more X-ray images, wherein the at least one image and the at least a second image correspond to 2-dimensional X-ray images providing different view angles measured with respect to a perpendicular to the plane; and
    tomographically processing the received first image and second image, said processing resulting in a processed X-ray image.

13. The system of claim 11, whether the means for storing is for storing the displacement values in a histogram.

14. The system of claim 11, wherein the rule is for determining whether the assembly meets a defined manufacturing tolerance.

15. The system of claim 11, the system further comprising means for autonomously providing a user indication as to a result of applying the rule.

16. The system of claim 11, wherein the means for autonomously determining the displacement values is configured for:
    determining a measured location for each of the portions of the assembly, with reference to the one or more directions of the plane;
    determining for each of the portions of the assembly an actual location with reference to the one or more directions of the plane; and
    determining for each of the portions of the assembly a difference between the measured and actual locations, the difference being indicative of the corresponding displacement value.

17. The system of claim 16, wherein the means for determining the displacement values is configured for determining the measured locations by determining for each of the portions of the assembly a centroid value of the portion.

18. The system of claim 16, wherein the means for determining the displacement values is configured for determining the actual locations by using a computer-aided design (CAD) specification of the assembly.

19. The system of claim 11,
    wherein the assembly is a ball grid array (BGA) assembly, and
    wherein the portions of the assembly correspond to solder balls of the BGA assembly.

* * * * *